United States Patent [19]
Ribier et al.

[11] Patent Number: 5,607,692
[45] Date of Patent: *Mar. 4, 1997

[54] DEPIGMENTING COMPOSITION FOR THE SIMULTANEOUS TREATMENT OF THE SURFACE LAYERS AND DEEP LAYERS OF THE SKIN, AND USE THEREOF

[75] Inventors: Alain Ribier; Jean-Thierry Simonnet; Chantal Fanchon, all of Paris; Laurence Arnaud-Sebillotte, Creteil; Evelyne Segot, Nogent Sur Marne, all of France

[73] Assignee: L'Oreal, Paris, France

[ * ] Notice: The term of this patent shall not extend beyond the expiration date of Pat. No. 5,601,841.

[21] Appl. No.: 366,739

[22] Filed: Dec. 30, 1994

[30] Foreign Application Priority Data

Dec. 30, 1993 [FR] France .................. 93 15870

[51] Int. Cl.⁶ .................. A61K 9/127; A61K 7/00
[52] U.S. Cl. .................. 424/450; 424/62; 424/401; 514/844
[58] Field of Search .................. 424/450, 401, 424/62; 514/844

[56] References Cited

U.S. PATENT DOCUMENTS 5,422,120  6/1995  Kim .................. 424/450

FOREIGN PATENT DOCUMENTS

A0559502  9/1993  European Pat. Off. ..
A2408387  6/1979  France .
WOA9315708  8/1993  WIPO .

OTHER PUBLICATIONS

International Journal Of Pharmaceutics, vol. 62, No. 1, 1990, NL pp. 75–79, Gabrijelcic et al. "Evaluation of liposomes as drug carriers into the skin by one-dimensional images".

Soap, Cosmetics, Chemical Specialties, vol. 69, No. 7, Jul. 1993 US, p. 77 "Formulation ideas".

Primary Examiner—Gollamudi S. Kishore
Attorney, Agent, or Firm—Oblon, Spivak, McClelland, Maier & Neustadt, P.C.

[57] ABSTRACT

A composition comprising a first dispersion of lipid vesicles which are capable of penetrating into the deep layers of the skin and which contain at least one active agent selected from the group consisting of anti-pigmenting agents, depigmenting agents and tyrosinase inhibitors, for treating these deep layers, and a second dispersion of lipid vesicles which are capable of penetrating into the surface layers of the skin and which contain at least one active agent selected from the group consisting of keratolytic agents, moisturizing agents and protective agents, for treating these surface layers, is found effective for depigmenting skin.

15 Claims, No Drawings

DEPIGMENTING COMPOSITION FOR THE SIMULTANEOUS TREATMENT OF THE SURFACE LAYERS AND DEEP LAYERS OF THE SKIN, AND USE THEREOF

BACKGROUND OF THE INVENTION

1. Field of the Invention

The invention relates to a cosmetic and/or dermatological composition intended for depigmenting the skin, or avoiding the pigmentation of the skin, both of the face and of the body, or even of the scalp. It relates more particularly to a composition comprising at least one active agent which is conveyed via at least two distinct types of lipid vesicles.

The invention also relates to the use of this composition for the cosmetic treatment of the skin, to the use of this composition for the preparation of an ointment intended for the dermatological treatment of the skin and to a cosmetic treatment process for the skin.

2. Discussion of the Background

At various times in their lives, some people develop darker patches on the skin and more especially on the hands, imparting a heterogeneity to the skin. In general, these patches are due to production of melanin on a considerable scale in the epidermis and/or the dermis of the skin.

These patches may be associated with several phenomena and more especially with ageing. In some cases, these patches may become cancerous. Thus, attempts are increasing to diminish, or even to eliminate, these patches.

Numerous depigmenting compositions exist on the market, but the effectiveness of these compositions, is, unfortunately, often insufficient.

Moreover, many examples are known of cosmetic or dermatological compositions intended for treating the skin, which have one or more active agents that are suitable for treating the skin and which are encapsulated in lipid spherules or vesicles (also known as liposomes).

Lipid spherules or vesicles are understood to refer to particles formed of a membrane consisting of one or more concentric lamellae, these lamellae containing one or more bimolecular layers of amphiphilic lipids encapsulating an aqueous phase. The aqueous phase may contain water-soluble active substances and the bimolecular layers of amphiphilic lipids may contain lipophilic active substances.

These spherules generally have a mean diameter of between 10 nm and 5,000 mn.

Among the many documents published regarding this matter there may be mentioned the French Certificate of Addition 2,408,387, which describes a composition based on aqueous dispersions of ionic or nonionic lipid spherules encapsulating at least one active substance. More precisely, this document describes compositions containing at least two dispersions of spherules containing different active agents, for the purpose of obtaining a mixed system, that is to say a system in which a first dispersion of spherules containing a first class of active substance is combined with a second dispersion of spherules containing another class of active substances, which enables the two types of substances to act simultaneously at the time of treatment and possibly to obtain a synergistic effect which would not be produced if these two types of substances were made to act successively and separately.

It is well known that the skin consists of surface layers, the stratum corneum, and of deep layers, the live epidermis and the dermis. Yet the specific delivery of such an active agent into the surface layers and, simultaneously, of the same or another active agent into the deep layers was not known in the prior art.

Thus there remains a need for the simultaneous treatment of both the surface and deep layers of the skin. There also remains a need for a composition of depigmenting skin in need thereof.

SUMMARY OF THE INVENTION

Accordingly one object of this invention is to provide a novel depigmenting or anti-pigmenting composition for the simultaneous treatment of the surface layers and deep layers of the skin comprising:

i) a first dispersion of lipid vesicles which are capable of penetrating into the deep layers of the skin and which contain at least one active agent selected from the group consisting of anti-pigmenting agents, depigmenting agents and tyrosinase inhibitors, for treating these deep layers; and ii) a second dispersion of lipid vesicles which are capable of penetrating into the surface layers of the skin and which contain at least one active agent selected from the group consisting of keratolytic agents, moisturizing agents and protective agents, for treating these surfaces layers.

According to the second object of the invention is to provide a composition for depigmenting skin.

According to a specific embodiment, the active agents contained in the first dispersion of vesicles and in the second are the same.

The inventors have now developed cosmetic and/or dermatological depigmenting or anti-pigmenting compositions which allow the simultaneous action of two different active agents and which furthermore allow these active agents to act in different areas of the skin, that is to say in the surface layers and in the deep layers of the skin, thereby very markedly enhancing the effectiveness of these compositions and the complementary or synergistic effect of the depigmenting active agents used.

The inventors have also developed cosmetic and/or dermatological depigmenting or anti-pigmenting compositions which enable the same active agent to act simultaneously in the surface layers and in the deep layers of the skin, providing a more complete and therefore a more effective treatment against the darker patches of the skin.

DETAILED DESCRIPTION OF THE PREFERRED EMBODIMENTS

The inventors have used a means of classifying vesicles which enables a person skilled in the art readily to select lipid vesicles capable of conveying the active agent to the deep layers of the skin, known as vesicles with deep-down action, and those capable of conveying the active agent to the surface layers of the skin, known as vesicles acting at the surface.

This classification is made on the basis of the diffusion constant D of a probe introduced into the vesicles. This probe is ASL [N-(1-oxyl-2,2,6,6-tetramethyl-4-piperidyl)-N,N-dimethyl-N-hydroxyethylammonium iodide], of formula:

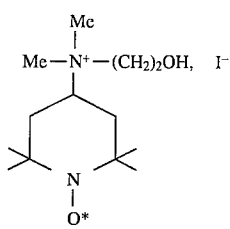

Vesicles for which the diffusion constant D of the probe in the stratum corneum is $>1\times10^{-7}$ cm$^2$ s$^{-1}$ are vesicles which are capable of penetrating into the deep layers of the skin.

Vesicles for which the diffusion constant D of the probe in the stratum corneum is $<1\times10^{-7}$ cm$^2$ s$^{-1}$ are vesicles which are capable of conveying the active agent within the surface layers of the skin.

The vesicles of the first type, the so-called vesicles with deep-down action, are generally in a fluid state at room temperature (about 20° C.), and those of the second type, the so-called vesicles acting at the surface, are generally in a gelled state at room temperature. The means of recognizing the state of the vesicles consists in determining the phase transition temperature (fluid-gel lamellar) of the main lipid constituting the membrane thereof, by differential thermal analysis (DTA).

Other characteristics of these vesicles relate to their ability to deliver the active agent to a greater or lesser depth in the skin. This is particularly the case for the degree of encapsulation.

Glucose is a labelling agent conventionally used for this type of determination (cf. in particular Liposomes a practical approach by R. R. C. New, IRL Press (1990), p. 125–136).

The degree of encapsulation is expressed as the volume of glucose solution encapsulated in the vesicles, measured in μl, based on the unit of weight (mg) of the lipids constituting the membrane. This degree of encapsulation is determined immediately after the step of separation of the free glucose and of the encapsulated glucose ($T_o$), as well as twenty-four hours after this separation ($T_{24\ hours}$).

The difference between these two successive determinations illustrates the permeability of the vesicles with respect to the encapsulated glucose, which may also be referred to as the encapsulation potential.

The first type of vesicles (delivering the active agent into the deep layers of the skin) has a high encapsulation potential for the small water-soluble molecules which are conventionally modelled by glucose, this encapsulation potential being maintained for at least 24 hours. The second category of vesicles (delivering the active agent into the surface layers of the skin) does not retain glucose in the encapsulated state for the same amount of time.

The main lipids constituting the vesicles of the first type (deep delivery of the active agent) are composed of at least one linear and saturated fatty chain with a length ranging from 16 to 30 carbon atoms, such as hydrogenated phospholipids (from plants or from egg), saturated synthetic phospholipids such an dipalmitoylphosphatidylcholine, and polyol alkyl ethers or polyol alkyl enters containing one, two or three fatty chains per molecule. These lipids are used alone or an a mixture.

The main lipids constituting the vesicles of the second type (active agent delivered at the surface) are chosen in particular from the group comprising ionic lipids such as, in particular, natural plant- or egg-based phospholipids, containing unsaturated fatty chains having from 16 to 30 carbon atoms; nonionic lipide such an, in particular, polyol alkyl ethers or polyol alkyl esters containing at least one fatty chain per molecule, including at least one fatty chain with a length of less than 16 carbon atoms, such as in lauryl polyglyceryl-6-cetearyl glycol other; as well an mixtures thereof. The latter is described in detail in Patent Application FR 92-09603 filed by L'Oréal.

It is possible, in a known manners to incorporate into the lipid phase constituting the lipid membrane of the vesicles at least one additive selected from the group consisting of the group formed from sterols (phytosterols, cholesterol or polyoxyethylenated phytosterols); long-chain alcohols, diols and triols (phytanetriol), long-chain amines and the quaternary ammonium derivatives thereof; phosphoric enters of fatty alcohols and the alkali metal (Na or K) salts thereof, such an dicetyl phosphate, sodium dicetyl phosphate, alkyl sulphates (sodium cetyl sulphate), alkali metal salts of cholesterol sulphate or of cholesterol phosphate, the sodium salt of phosphatidic acid, and lipoamino acids and the salts thereof such as the sodium acylglutamates.

Examples of vesicles of the first category (delivering the active agent into the deep layers of the skin) which nay be mentioned are vesicles obtained from the following lipids (CTFA name):

A/cholesterol/casein lipoamino acid, especially in 45/45/10 weight ratio (where A is a triglyceryl cetyl ether marketed by the company Chimex under the name CHIMEXANE NL);

B/cholesterol/dicetyl phosphate, especially in a 60/35/5 weight ratio (where B is a mixture of triglyceryl mono-, di- and tricetyl ether, marketed by the company Chimex under the name CHIMEXANE NT);

Span 40 (from ICI, or sorbitan palmitate)/cholesterol/sodium acylglutamate (marketed under the name HS11 by the company Ajinomoto), especially in a 47.5/47.5/5 weight ratio;

PEG 8 stearate/cholesterol/sodium acylglutamate, especially with a 47.5/47.5/5 weight ratio (where PEG 8 stearate is polyethylene glycol containing 8 units of ethylene oxide, marketed by Unichema under the name PEG 400 stearate);

PEG 8 stearate/cholesterol/phytanEtriol/sodium acylglutamate, especially with a 47.5/20/27.5/5 weight ratio;

Hydrogenated lecithin/polyoxyethylenated phytosterol containing 5 units of ethylene oxide, especially in a 60/40 weight ratio;

Polyoxyethylenated methylglucose distearate containing 20 units of ethylene oxide/cholesterol/sodium acylglutamate, especially in a 45/45/10 weight ratio (the distearate being, for example, that marketed under the name GLUCAM E 20 distearate by Amerchol);

A/cholesterol/dicetyl phosphate, especially with a 47.5/47.5/5 weight ratio (where A is a triglyceryl cetyl ether marketed by the company Chimex under the name CHIMEXANE NL);

Diglyceryl distearate (for example that marketed by Nihon under the name EMALEX DS G2)/cholesterol/sodium acylglutamate, in a 45/45/10 weight ratio;

Sucrose mono- and distearate (for example GRILLOTEN PSE 141 G from Grillo)/cholesterol/sodium acylglutamate, especially in a 45/45/10 weight ratio;

Tetraglyceryl tristearate (for example TETRAGLYN 3S from Nikkol)/cholesterol/sodium acylglutamate, especially in a 45/45/10 weight ratio.

Examples of vesicles of the second category (delivering the active agent into the surface layers of the skin) which may be mentioned are vesicles obtained from the following lipids:

Sunflower lecithin;

NATIPIDE II (soya lecithin/ethanol/water in a 20/16/64 weight ratio, marketed by Nattermann);

C (soya lecithin/cholesterol/propylene glycol in a 60/20/20 weight ratio, marketed by Nattermann under the name NAT 50 PG);

D/dimyristyl phosphate, especially in a 95/5 weight ratio (where D is a lauryl polyglyceryl-6-cetearyl glycol ether marketed by Chimax under the name CHIMEXANE NS).

Table I below gives, for some of the vesicles obtained using the above lipids, the diffusion constant D for ASL in the stratum corneum and in the epidermis/dermis, as well an the degree of encapsulation of glucose and the phase transition temperature of the main lipid constituting the membrane. The diffusion constant was measured for an encapsulated ASL concentration of 0.35% by weight based on the total weight of the composition.

reduction kinetic imaging" by V. Gabrijelcic et al., Periodicum Biologorum vol. 93, No. 2, p. 245–246, (1991).

Measurement of the degree of encapsulation is carried out as described in "Liposomes a practical approach" by R. R. C. New, IRL Press (1990), p. 125–136, and that of the phase transition temperature is carried out as described above.

The active agents with deep-down action and the active agents acting at the surface are those which are conventionally used in the cosmetic and dermatological fields.

The protective agents delivered at the surface are, in particular, UV-A and/or UV-B screening agents, pigments or nanopigments.

Sunscreen agents which may be mentioned as a guide are: p-aminobenzoic acid and the derivatives (glyceryl, ethyl and isobutyl esters); anthranilates (such an o-aminobenzoic acid or the alkyl esters thereof); salicylates (amyl, phenyl, benzyl or dipropylene glycol esters); cinnamic acid derivatives (amyl and benzyl esters); dihydroxycinnamic acid derivatives (umbelliferone); trihydroxycinnamic acid derivatives (esculetin); hydrocarbons (stilbene); dibenzalacetone and benzalacetophanone; coumarin derivatives; hydroxy- or methoxy-substituted benzophenones; tannic acid and the

TABLE I

| Ref. | LIPID SYSTEMS | Proportions % by weight (mg) | Diffusion coefficient D in $10^{-7}$ $cm^2$ $s^{-1}$ in the stratum corneum | in the epidermis/dermis | Degree of encapsulation of glucose in μl/mg $T_o$ | $T_{24h}$ | Phase transition temperature in °C. |
|---|---|---|---|---|---|---|---|
| | 1st type - deep down | | | | | | |
| 1 | A/cholesterol/casein lipoamino acid | 45/45/10 (67.5/67.5/15) | 42 | 5 | 7.5 | 6.8 | 50 |
| 2 | B/cholesterol/dicetyl phosphate | 60/35/5 (90/52.5/7.5) | 58 | 2 | 11.1 | 11.1 | 54 |
| 3 | Span 40/cholesterol/ sodium acylglutamate | 47.5/47.5/5 (71.25/71.25/7.5) | 42 | 2 | 13.8 | 13.8 | 50 |
| 4 | PEG 8 stearate/ cholesterol/sodium acylglutamate | 47.5/47.5/5 (71.25/71.25/7.5) | 42 | 2 | 14.4 | 14.4 | 55 |
| 5 | PEG 8 stearate/ cholesterol/phytanetriol/ sodium acylglutamate | 47.5/20/27.5/5 (71.25/30/ 41.25/7.5) | 8.3 | 2.5 | 4.1 | 3.0 | 55 |
| 6 | Hydrogenated lecithin/ polyoxyethylenated phytosterol | 60/40 (90/60) | 8 | 2 | 6.0 | 4.8 | 80 |
| | 2nd type - surface | | | | | | |
| 7 | Sunflower lecithin | 100 (150) | 0.3 | 0.2 | 1.6 | 0 | <0 |
| 8 | Natipide II (soya lecithin/ethanol/water) | 20/16/64 (30/24/96) | 0.4 | 0.2 | 0.4 | 0 | <0 |
| 9 | C (soya lecithin/ sterols/propylene glycol) | 60/20/20 (90/30/30) | 0.25 | 0.1 | 1.8 | 0 | <0 |
| 10 | D/dimyristyl phosphate | 95/5 (142.5/7.5) | 0.3 | 0.2 | 2.0 | 0 | 14 |

Measurement of the diffusion constant D is carried out by combining two methods using a paramagnetic probe, ASL: one-dimensional and periodic electron paramagnetic resonance (EPR), on the one hand, and EPR kinetic imaging, on the other hand. These two methods are described respectively in the articles "Evaluation of liposomes as drug carriers into the skin by one-dimensional EPR imaging" by V. Gabrijelcic at al., International Journal of Pharmaceutics, 62 (1990) p. 75–79, Elsevier, and "Liposome-entrapped molecules penetration into the skin measured by nitroxide derivatives thereof; benzophenones and any other sunscreen agents which are conventionally used in the cosmetic and/or dermatological field, such an benzylidenecamphor, benzene-1,4-di(3-methylidene-10-camphorsulphonic) acid, referred to as deep active agent, or alternatively 4-(3-methylidenecamphor)phenyltrimethylammonium methyl sulphate, 2-ethylhexyl cyano-3,3'-diphenylacrylate, and dibenzoylmethane, as well as the mixtures thereof.

As pigments or nanopigments, there may be mentioned zinc oxide and/or titanium oxide ($TiO_2$, $Zno_2$).

As keratolytic agents, there may be mentioned salicylic acid and the derivatives thereof, such as n-octanoylsalicylic acid; retinoic acid; urea; resorcinol; alpha-hydroxy acids, such as lactic acid, malic acid and glycolic acid, and acids from fruit (citric acid).

As moisturizing agents, there may be mentioned polyhydroxylated alcohols such as sorbitol, glycerine, hexanetriol, propylene glycol, hexylene glycol and polyethylene glycol; sugars (fructose and galactose) and the derivatives thereof; starches and the derivatives thereof; d-panthenol; hyaluronic acid; monoethanolamine lactamide and monoethanolamine acetamide; 2-pyrrolidone-5-carboxylic acid; and also urea, as well as mixtures of these moisturizing agents.

The active agents encapsulated in the vesicles with deep-down action are those which are conventionally used in cosmetics and in particular kojic acid; caffeic acid; retinoic acid; hydroquinone and the derivatives thereof, such as benzylhydroquinone ether; ascorbic acid and the derivatives thereof, such as magnesium ascorbyl phosphate; extracts of plants such an, for example, licorice, mulberry, heather and angelica (ashitaba); pearl extracts; steroidal anti-inflammatory agents of hydrocortisone type and the like; nonsteroidal anti-inflammatory agents selected from the group consisting of aspirin (acetylsalicylic acid), acetaminophen, naproxen and fenamic acid derivatives such as the sodium salt; anti-inflammatory agents such as alphabisabolol, β-glycyrrhetinic acid and allantoin an well as mixtures of these active agents. These anti-inflammatory agents promote depigmentation of the skin in particular when they are associated with a depigmenting or anti-pigmenting agent.

Advantageously, several active agents are used simultaneously in each type of vesicles, these active agents having the same function and/or imparting to the skin, at the surface and deep down, the same type of effect; the agents acting at the surface and the agents with deep-down action are thus complementary.

The agents acting at the surface and the agents with deep-down action may represent from 0.05% to 10% by weight based on the total weight of the composition.

The compositions according to the invention may be provided in all the pharmaceutical forms normally used for topical application, such an aqueous gels, emulsions, lotions, ointments, sera and, more particularly, vesicle-dispersed oil droplets such as those described in French Patents FR-A-2,485,921 and FR-A-2,490,504.

As is known, in addition to the vesicles, a vegetable oil, mineral oil, silicone-containing oil or synthetic oil which in dispersed in an aqueous phase, and also hydrophilic adjuvants such as gelling agents, preserving agents, opacifying agents, lipophilic adjuvants such as fragrances, pigments and fillers, may be found in the compositions of the invention, as described in the above French patents. The dispersed oil may represent from 2% to 40% by weight based on the total weight of the compositions and the adjuvants may represent from 0.1% to 10% by weight in total.

Another subject of the invention is the use of the composition defined above for the depigmenting or anti-pigmenting cosmetic treatment of the skin of the face and/or of the body, an well as for the preparation of an ointment intended for treating skin patches of pathological origin.

Another subject of the invention in a cosmetic treatment process for depigmenting or anti-pigmenting the skin, consisting in applying the composition defined above to the skin.

The total weight of vesicle contained in the composition is preferably from 1 to 90 wt. %, more preferably from 5 to 70 wt. %, most preferably from 5 to 20 wt. % based on the total weight of the composition.

The ratio of the amount of vesicles of the first dispersion type which are capable of penetrating into the deep layers to the second dispersion type which are capable of penetrating into the surface layers is preferably from 1:9 to 9:1, more preferably from 3:7 to 7:3, most preferably from 4:6 to 6:4.

Within the context of the following examples the term qs 100 g is an amount needed to bring the total amount of the composition to 100 g.

Other characteristics and advantages of the invention will emerge more clearly from the description, given as an illustration and with no limitation being implied, which follows.

A) Production of Lipid Vesicles Containing ASL

The constituent lipids of the wall of the vesicles are weighed out and dissolved in 10 ml of methanol. The alcoholic solution in then transferred into a 50 ml round-bottomed flank with a ground joint, which is subsequently placed on a rotary evaporator such that the contents are thermostatted at a temperature of 30° C. The evaporation in continued until a dry film of lipids in deposited on the wall of the flask.

3 ml of a 0.01 molar aqueous solution of ASL are then added to the flank, which in subsequently shaken by hand for about 10 minutes either at room temperature (20° C.) for the vesicles of Table I of reference nos. 7 to 10, or at a temperature of 50° C. for the vesicles of reference nos. 1 to 6 of Table I. The medium is then left to equilibrate at room temperature for 2 hours, after which the dispersion in placed in a dialysis bag and in contact with 500 ml of distilled water. Dialysis takes place overnight. The next day, the water is changed and the dialysis is continued for a further 4 hours.

A cotton thread 0.3 mm thick is then soaked in the vesicle dispersion and then placed in contact with section of skin cut from a pig's ear which has been freshly taken from an abattoir intended for food supply.

The ear sample taken is rinsed with water and cut into slices 1 mm thick, 5 mm wide and 10 mm long and then placed in a maintenance cell. Measurements of the diffusion of ASL into the skin are made in the 24 hours following the taking of the skin sample.

B) Production of the Cosmetic Composition

1- Production of Vesicles of the First Type Diffusing Deep Down)

The vesicles (with deep-down action) are prepared according to a usual method of co-fusion of the various membrane constituents (see Table I) chosen. Thus, the membrane constituent having the lowest melting point $T_m$ is melted. The other membrane constituents are added thereto and the mixture in then homogenized with moderate stirring and is finally partially hydrated, while maintaining the melting temperature $T_m$ defined above.

An aqueous solution of at least one first active agent for the deep-down treatment is added to the paste obtained. The mixture is stirred with at least one first active agent for the deep-down treatment is added to a turbine for 1 h 30 min in order to hydrate fully, while maintaining the temperature $T_m$. One or more other active agents for the deep-down treatment are added to the reaction medium, homogenization is carried out and the temperature of the medium is lower to room temperature (20° C.).

2- Production of Vesicles of the Second Type (Diffusing at the Surface)

An aqueous solution of one (or more) second active agents for the surface treatment is introduced, at room temperature (20° C.) and with simple stirring, into the chosen mixture of constituents which are to form the membrane of the vesicles acting at the surface (see Table I). Vesicles acting at the surface encapsulating the second active agent acting at the surface are thus obtained.

3- Production of the "Double-Liposome" Composition

The fatty phase (the oils) of the composition is added to the medium containing the vesicles with deep-down action and it is dispersed (at room temperature) with stirring. The reaction medium obtained is then mixed with that containing the vesicles acting at the surface. The adjuvants, such as preserving agents, a gelling agent which may be neutralized if necessary with a base (triethanolamine or sodium hydroxide), and fragrances, etc., are then optionally added.

The product obtained is in the form of a soft and smooth white cream which may be used in the cosmetic and/or dermatological field for depigmenting the skin at the surface and deep down. This cream may be used daily. Specific examples of cosmetic and/or dermatological depigmenting compositions in accordance with the invention are given below. The compositions are given in % by weight.

EXAMPLE 1

Depigmenting Double-Liposome Cream

| - Preparation A/Liposomes with deep-down action: | | |
|---|---|---|
| Triglyceryl cetyl ether | | 7.6 g |
| Cholesterol | | 7.6 g |
| Sodium acylglutamate | | 0.8 g |
| Kojic acid (active agent) | | 2.0 g |
| Glycerol (active agent) | | 12.0 g |
| Preserving agents | | 0.1 g |
| Demineralized water | qs | 100 g |
| - Preparation B: Liposomes acting at the surface: | | |
| CHIMEXANE NS/dimyrietyl phosphate in a 95/5 weight ratio | | 20.0 g |
| 5-n-Octanoylsalicylic acid (active agent) | | 2.0 g |
| glycerol (active agent) | | 15 g |
| Preserving agent | | 0.2 g |
| Demineralized water | qs | 100 g |
| - Double-liposome composition: | | |
| Preparation A | | 31.3 g |
| Preparation B | | 25.0 g |
| Vegetable oil | | 3.0 g |
| Volatile silicone oil | | 4.5 g |
| Preserving agents | | 0.3 g |
| Sodium hydroxide | | 1.8 g |
| Carboxyvinyl polymer (gelling agent) | | 0.9 g |
| Demineralized water | qs | 100 g |

EXAMPLE 2

Depigmenting Double-Liposome Cream

This cream differs from that of Example 1 in that salicylic acid in used as active agent acting at the surface instead of 5-n-octanoylsalicylic acid.

EXAMPLE 3

Depigmenting Double-Liposome Cream

| - Preparation A: Liposomes with deep-down action: | | |
|---|---|---|
| PEG 8 stearate | | 7.6 g |
| Cholesterol | | 7.6 g |
| Sodium acylglutamate | | 0.8 g |
| Hydroquinone (active agent) | | 1.0 g |
| methylparaben (preserving agent) | | 0.1 g |
| Demineralized water | qs | 100 g |
| - Preparation B: Liposomes acting at the surface: | | |
| CHIMEXANE NS | | 18.0 g |
| Dimyristyl phosphate | | 2.0 g |
| Deep active agent | | 2.0 g |
| Triethanolamine | | 1.0 g |
| Glycerine (active agent) | | 15.0 g |
| Methylparaben (preserving agent) | | 0.2 g |
| Demineralized water | qs | 100 g |
| - Double-liposome composition: | | |
| Preparation A | | 31.3 g |
| Preparation B | | 20.8 g |
| Vegetable oil | | 8.0 g |
| Carboxyvinyl polymer | | 0.9 g |
| Sodium hydroxide | | 1.8 g |
| Preserving agents | | 0.5 g |
| Demineralized water | qs | 100 g |

Obviously, numerous modifications and variations of the present invention are possible in light of the above teachings. It is therefore to be understood that within the scope of the appended claims, the invention may be practiced otherwise than as specifically described herein.

This application is based on French Patent Application 93/15870, filed with the French Patent Office on Dec. 30, 1993, the entire contents of which are hereby incorporated by reference.

What is claimed as new and desired to be secured by Letters Patent of the United States is:

1. A depigmenting or anti-pigmenting composition for simultaneous treatment of the layers of the stratum corneum and deep layers of the skin, comprising a dispersion mixture of:

i) a first dispersion of lipid vesicles which are capable of penetrating into said deep layers of the skin and which contain at least one active agent selected from the group consisting of anti-pigmenting agents and depigmenting, agents, for treating said deep layers; and ii) a second dispersion of lipid vesicles which are capable of penetrating into said layers of the stratum corneum of the skin and which contain at least one active agent selected from the group consisting of keratolytic agents, moisturizing agents and protective agents, for treating said layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1 \times 10^{-7}$ cm$^2$/s and in that said vesicles of said second dispersion ensure a distribution of ASL in the stratum corneum $<1 \times 10^{-7}$ cm$^2$/s.

2. The composition of claim 1, wherein said vesicles of said first dispersion are in a fluid state at room temperature and said vesicles of said second dispersion are in a gelled state at room temperature.

3. The composition of claim 1, wherein said vesicles of said first dispersion provide an encapsulation potential of glucose for at least 24 hours, and said vesicles of said second dispersion provide an encapsulation potential of glucose for less than 24 hours.

4. The composition of claim 1, wherein said vesicles of said first dispersion are formed of lipids having at least one linear and saturated fatty chain having from 16 to 30 carbon atoms.

5. The composition of claim 1, wherein said vesicles of said first dispersion are formed of at least one lipid selected from the group consisting of natural ionic phospholipids, saturated synthetic phospholipids, polyol alkyl ethers containing at least one linear fatty chain, polyol alkyl esters containing at least one fatty chain and a mixture thereof.

6. The composition of claim 1, wherein said vesicles of said first dispersion are formed of lipids selected from the group consisting of:

triglyceryl cetyl ether, cholesterol, and casein lipoamino acid;

a mixture of triglyceryl mono-, di- and tricetyl ether, cholesterol, and dicetyl phosphate;

triglyceryl cetyl ether, cholesterol, and dicetyl phosphate;

sorbitan palmitate, cholesterol, and sodium acylglutamate;

PEG 8 stearate, cholesterol, and sodium acylglutamate;

diglyceryl distearate, cholesterol, and sodium acylglutamate;

sucrose mono- and distearate, cholesterol, and sodium acylglutamate;

PEG 8 stearate, cholesterol, phytanetriol, and sodium acylglutamate;

polyoxyethylenated methylglucose distearate containing 20 mol of ethylene oxide, cholesterol, and sodium acylglutamate;

hydrogenated lecithin, and polyoxyethylenated phytosterol; and tetraglyceryl tristearate, cholesterol, and sodium acylglutamate.

7. The composition of claim 1, wherein said vesicles of said second dispersion are formed of lipids selected from the group consisting of natural ionic phospholipids having unsaturated fatty chains having from 16 to 30 carbon atoms, polyol alkyl ethers having at least one fatty chain per molecule, comprising at least one fatty chain with a length of less than 16 carbon atoms, polyol alkyl esters having at least one fatty chain per molecule, comprising at least one fatty chain with a length of less than 16 carbon atoms.

8. The composition of claim 1 wherein said vesicles of said second dispersion are formed of at least one lipid selected from the group consisting of sunflower lecithin; soya lecithin, ethanol, and water; soya lecithin, cholesterol, and propylene glycol; and lauryl polyglyceryl-6-cetearyl glycol ether and dimyristyl phosphate.

9. The composition of claim 1, wherein said active agent of said first dispersion and said active agent of said second dispersion provide the same function, the same effect or both.

10. The composition of claim 1, wherein said active agent of said first dispersion and said active agent of said second dispersion are the same.

11. The composition of claim 1 wherein said active agent contained in said first dispersion is selected from the group consisting of kojic acid, retinoic acid, caffeic acid, a hydroquinone, an ascorbic acid, plant extracts, pearl extracts, anti-inflammatory agents, and a mixture thereof.

12. The composition of claim 1 wherein said active agent contained in said second dispersion is selected from the group consisting of salicylic acid, 5-n-octanoylsalicylic acid, urea, resorcinol, an α-hydroxy acid, retinoic acid, hyaluronic acid, a sunscreen agent, a pigment, a polyhydroxylated alcohol, a sugar, a starch, and a mixture thereof.

13. The composition of claim 1, further comprising iii) an oily phase which is dispersed in an aqueous phase.

14. The composition of claim 1, further comprising iv) hydrophilic adjuvants or lipophilic adjuvants.

15. A method for depigmenting or anti-pigmenting the skin, comprising applying to the skin of a patient in need thereof, an effective amount of a composition comprising a dispersion mixture of:

i) a first dispersion of lipid vesicles which are capable of penetrating into the deep layers of said skin and which contains at least one active agent selected from the group consisting of anti-pigmenting agents, depigmenting agents and tyrosinase inhibitors, for treating said deep layers; and ii) a second dispersion lipid of vesicles which are capable of penetrating into the layers of the stratum corneum of said skin and which contains at least one active agent selected from the group consisting of keratolytic agents, moisturizing agents and protective agents, for treating said layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10-7$ cm$^2$/s.

* * * * *

UNITED STATES PATENT AND TRADEMARK OFFICE
CERTIFICATE OF CORRECTION

PATENT NO. : 5,607,692
DATED : March 4, 1997
INVENTOR(S) : Alain RIBIER, et al.

It is certified that error appears in the above-indentified patent and that said Letters Patent is hereby corrected as shown below:

On the title page, Item [*], the Terminal Disclaimer Information is incorrect. It should read:

-- [*] Notice: The term of this patent shall not extend beyond the expiration date of Pat. No. 5,601,833. --

Signed and Sealed this

Eighth Day of July, 1997

*Attest:*

BRUCE LEHMAN

*Attesting Officer*  Commissioner of Patents and Trademarks